United States Patent [19]

Strom

[11] 4,397,785
[45] Aug. 9, 1983

[54] PREPARATION OF 3,3'5,5'-TETRATERTIARY BUTYL DIPHENOQUINONE

[75] Inventor: Robert M. Strom, Midland, Mich.

[73] Assignee: The Dow Chemical Company, Midland, Mich.

[21] Appl. No.: 248,384

[22] Filed: Mar. 27, 1981

[51] Int. Cl.³ .............................................. C07C 97/18
[52] U.S. Cl. ................................................. 260/396 N
[58] Field of Search .................. 260/396 N; 568/730, 568/805

[56] References Cited

U.S. PATENT DOCUMENTS

| | | | |
|---|---|---|---|
| 2,900,417 | 8/1959 | Filbey et al. | 568/730 |
| 3,153,098 | 10/1964 | Boag | 568/730 |
| 3,306,875 | 2/1967 | Hay | 521/25 |
| 3,555,052 | 1/1971 | Yonemitsu et al. | 260/396 N |
| 3,562,338 | 2/1971 | Zaweski | 260/396 N |
| 3,631,208 | 12/1971 | Hay | 260/396 R |
| 3,720,721 | 3/1973 | Becker et al. | 568/730 |
| 3,804,864 | 4/1974 | Rutledge | 260/396 R |
| 3,804,865 | 4/1974 | Rutledge | 260/396 N |
| 3,825,521 | 7/1974 | Izawa et al. | 528/215 |
| 4,086,253 | 4/1978 | Hopper et al. | 260/396 N |
| 4,180,686 | 12/1979 | Dodd | 568/730 |
| 4,205,187 | 5/1980 | Cardenas et al. | 568/805 |

OTHER PUBLICATIONS

Finkbeiner, H., et al., "Polymerization by Oxidative Coupling", *Journal of Organic Chemistry*, vol. 31, Feb. 1966, pp. 549–555.

*Primary Examiner*—Delbert E. Gantz
*Assistant Examiner*—Raymond Covington
*Attorney, Agent, or Firm*—Douglas N. Deline

[57] ABSTRACT

Oxidative coupling products of 2,6-ditertiary butyl phenol are formed by contacting the 2,6-ditertiary butyl phenol with an oxygen-containing gas in the presence of a heterogeneous oxidative coupling catalyst in methanol.

6 Claims, No Drawings

PREPARATION OF 3,3'5,5'-TETRATERTIARY BUTYL DIPHENOQUINONE

BACKGROUND OF THE INVENTION

The present invention relates to an improved process for the preparation of 3,3',5,5'-tetratertiary butyl diphenoquinone by the oxidative coupling of 2,6-ditertiary butyl phenol. More particularly the invention lies in the discovery that the catalytic oxidative coupling of 2,6-ditertiary butyl phenol is surprisingly improved if the reaction is conducted in methanol.

The oxidative coupling of phenols, including 2,6-ditertiary butyl phenol is a known reaction. Numerous catalysts and process conditions have been suggested by the art. U.S. Pat. No. 3,555,052, published Jan. 12, 1971, disclosed that reduced noble metals were suitable catalysts for the oxidative coupling of phenols in the presence of oxygen to form diphenoquinone or polyarylene ethers. Suitable solvents included t-butyl and t-amyl alcohol.

3,3',5,5'-Tetratertiary butyl diphenoquinone is a useful antioxidant. It is also a valuable intermediate for the production of 2,2',6,6'-tetratertiary butyl-p,p'-biphenol a useful stabilizer and antioxidant. Furthermore, the 2,2',6,6'-tetratertiary butyl-p,p'-biphenol may be dealkylated to give p,p'-biphenol which is useful in the synthesis of polymers, especially polyesters.

SUMMARY OF THE INVENTION

The present invention comprises an improved process for formation of 3,3',5,5'-tetratertiary butyl diphenoquinone by the oxidative coupling of 2,6-ditertiary butyl phenol by contacting the same with a heterogeneous dehydrogenation catalyst under oxidizing conditions in a liquid reaction medium comprising methanol. The 3,3',5,5'-tetratertiary butyl diphenoquinone may be reduced to the corresponding 2,2',6,6'-tetratertiary butyl-p,p'-biphenol as is known in the art. Further, the 2,2',6,6'-tetratertiary butyl-p,p'-biphenol may be dealkylated to yield p,p'-biphenol. The dealkylation reaction is acomplished by known techniques, for example, heating the 2,2',6,6'-tetratertiary butyl-p,p'-biphenol, preferably in the presence of an acid.

DETAILED DESCRIPTION OF THE INVENTION

The heterogeneous oxidative coupling catalysts employed in the instant invention are solids which are substantially non-leachable in the reaction medium and capable of producing carbon-carbon coupled reaction products under the conditions herein employed. Suitable catalysts are metals of groups VIII and IB of the Periodic Table along with chromium, molybdenum, zinc or mixtures thereof present in a valence suitable for forming oxidatively coupled reaction products. Generally, these catalysts under the conditions of the invention exist in active catalytic specie as the corresponding metal oxides. Preferred catalysts are those containing noble metals, particularly platinum or palladium.

The catalyst is preferably employed in highly commutated or dispersed form so as to provide as large a surface area as possible for catalytic reaction. The catalyst may be deposited onto a support, preferably one of high surface area in order to produce the desired highly dispersed form. Alternatively, certain of the catalysts, for example, copper chromite, may be treated in known manner to produce a self-supporting porous crystalline catalyst of high surface area.

In the operation of the invention, 2,6-ditertiary butyl phenol mixed with methanol is contacted with the previously described heterogeneous oxidative coupling catalyst in the presence of oxygen and preferably under elevated pressure. The oxygen may be air or oxygen itself. Pressures from about atmospheric to about 1000 psig may be employed. Most preferred pressures are from about 100 to about 500 psig.

The reaction is performed at elevated temperatures. Suitable temperatures are from about 30° C. to about 200° C. Preferred temperatures are from about 50° C. to about 100° C.

The reaction product is readily recovered from the reaction by precipitation. Purification, if desired, may be accomplished by reprecipitation from an organic solvent such as benzene or toluene. Generally, however, the product is recovered in high yield and purity directly from the reaction mixture. Further purification is not usually required.

The reduction of the 3,3',5,5'-tetratertiary butyl diphenoquinone to 2,2',6,6'-tetratertiary butyl-p,p'-biphenol may be accomplished by catalytic reduction in the presence of a heterogeneous reduction catalyst. The step is accomplished under reducing conditions, for example, by contacting the 3,3',5,5'-tetratertiary butyl diphenoquinone in a suitable solvent including methanol or an aromatic liquid with the heterogeneous reduction catalyst in the presence of a hydrogen-containing gas at elevated temperatures and pressures. Suitable temperatures are from about 25° C. to about 200° C. and preferably about 50° C. to about 160° C. Pressures from about atmospheric to about 100 psig may suitably be employed.

The heterogeneous reduction catalysts employed in the reduction operation may be those catalysts corresponding to the oxidative coupling catalysts initially employed, excepting that under the conditions of the reduction, the species responsible for the reaction may differ from the species responsible for the oxidative coupling reaction.

For example, it has been previously stated that in the case of the noble metals, the corresponding noble metal oxide is an effective oxidative coupling catalyst under the conditions herein employed. Under the conditions for reduction in the presence of a hydrogen gas, the active catalytic species is instead the reduced metal.

Copper chromite catalysts are similarly capable of selective hydrogenation or dehydrogenation reactions depending on reaction conditions and catalyst valence. When in a high valence, the catalysts are hydrogenation catalysts. Upon reduction, they become dehydrogenation catalysts. The reduction may occur in situ as, for example, by exposure to the instant reducing medium during the reduction reaction.

Many catalysts contain additional elements intended to stabilize the catalyst. For example, in copper chromite catalysts, barium is sometimes added in order to prevent reduction of the catalyst during hydrogenation reactions.

Included in the invention, however, are all heterogeneous catalysts capable of reducing the 3,3',5,5'-tetratertiary butyl diphenoquinone to 2,2',6,6'-tetratertiary butyl-p,p'-biphenol. Preferred are such catalysts containing a metal of Group VIII and IB of the Periodic Table along with chromium, molybdenum and zinc, present in a valence state capable of reducing 3,3',5,5'-tetratertiary butyl diphenoquinone. The catalyst, however, may contain the aforementioned metals in more than one oxidation state, e.g., as a mixture of the elemental metal and various metal oxides of the same or different metal. The catalysts under the conditions of the reaction are suitably maintained in a valence capable of effecting the catalytic reduction of the diphenoquinone. Most preferred are noble metal-containing catalysts, said noble being maintained in a suitable valence.

Alternatively, instead of employing the hydrogen-containing gas in the reduction, high yields of the desired 2,2',6,6'-tetratertiary butyl-p,p'-biphenol may be produced if the 3,3',5,5'-tetratertiary butyl diphenoquinone is contacted with 2,6-ditertiary butyl phenol in the presence of a basic catalyst, for example, pyridine, caustic or alkali metal carbonate.

Accordingly, a solution of 2,6-ditertiary butyl phenol may be partially reacted under the oxidative coupling conditions previously described to about one-half completion or more. At this point, additional 2,6-ditertiary butyl phenol may be added to the reaction mixture such that about 2 moles of 2,6-ditertiary butyl phenol are present for each mole of diphenoquinone. The reaction mixture is thereafter heated in the substantial absence of oxygen in the presence of the above basic catalysts wherein the remaining uncoupled 2,6-ditertiary butyl phenol and the 3,3',5,5'-tetratertiary butyl diphenoquinone react together to result in formation of the desired 2,2',6,6'-tetratertiary butyl-p,p'-biphenol. Extra hydrogen gas is not required for the reaction. The process is already known having been previously described in U.S. Pat. No. 3,631,208. A third and previously unappreciated method of conducting the reduction is to contact the 3,3',5,5=-tetratertiary butyl diphenoquinone with 2,6-ditertiary butyl phenol in methanol. No catalyst needs to be employed. In other respects the reduction is conducted as previously described in the above U.S. Pat. No. 3,631,208.

Any of the above-described methods of effecting reduction of the diphenoquinone may be employed.

As previously explained the 2,2',6,6'-tetratertiary butyl-p,p'-biphenol may easily be dealkylated if desired. One suitable means of accomplishing the dealkylation is to contact the 2,2',6,6'-tetratertiary butyl-p,p'-biphenol with a dealkylation agent such as a strong acid, for example, a strong mineral acid or strong organic acid, e.g., p-toluene sulfonic acid. A solid acid such as an acid ion-exchange resin may also be employed.

SPECIFIC EMBODIMENTS

The following examples are provided as further illustrative of the invention and are not to be construed as limiting. Unless otherwise indicated, results are expressed in percent by weight.

EXAMPLE 1

To a stainless steel pressure reactor equipped with a heating mantle and mechanical stirrer were added 2,6-ditertiary butyl phenol (25 g), a 5 percent palladium on carbon catalyst obtained commercially from Engelhard Minerals and Chemicals Corporation (0.125 g), and 50 ml of the solvents identified in Table I. Analysis of a sample of the catalyst by Electron Spectroscopy for Chemical Analysis (ESCA) according to recognized methods of analysis indicated the catalyst surface consisted substantially of palladium oxide.

The reactor was then sealed, pressurized to about 250 psig with oxygen gas and heated to the temperature indicated in Table I. In addition to the above listed compounds in the runs employing methanol and isopropyl alcohol, a small amount (approx. 0.1 g) of sodium carbonate was also present.

After completion of the reaction the mixture was analyzed by gas-liquid chromatography to determine the amount of product 3,3',5,5'-tetratertiary butyl diphenoquinone formed. Also determined was the amount of reduced product 2,2',6,6'-tetratertiary butyl biphenol and the amount of co-product 2,6-ditertiary butyl-1,4-benzoquinone. Results are contained in Table I.

TABLE I[1]

| Run | Solvent | Temp (°C.) | Time (min.) | DQ[2] | BP[3] | BQ[4] |
|---|---|---|---|---|---|---|
| 1 | methanol | 60 | 40 | 16.0 | 1.2 | 0.6 |
| 2 | methanol | 60 | 115 | 65.0 | 2.6 | 0.8 |
| 3 | isopropanol | 60 | 150 | 0.6 | 0.6 | — |
| 4 | isopropanol | 60 | 285 | 1.4 | 0.8 | — |
| 5 | t-butanol | 60 | 40 | 0.04 | 0.3 | 0.7 |
| 6 | benzene | 60 | 240 | 7.8 | 1.2 | 1.1 |
| 7 | o-dichlorobenzene | 150 | 120 | 11.8 | — | — |

[1]Amount of reactant remaining is not indicated.
[2]3,3',5,5'-tetratertiary butyl diphenoquinone product.
[3]2,2',6,6'-tetratertiary butyl-p,p'-biphenol product.
[4]2,6-ditertiary butyl-1,4-benzoquinone by-product.

It may be seen that surprisingly the use of other lower alcohols exemplified by isopropanol, does not give equivalent results to the use of methanol in combination with the heterogeneous oxidative coupling catalyst.

EXAMPLE 2

The reaction conditions of Example 1 were substantially repeated employing an amorphous palladium oxide on carbon catalyst produced by evaporating a basic aqueous solution of a water-soluble palladium salt having powdered charcoal added thereto. The powdered charcoal having a surface coating of palladium hydroxide was recovered and heated at 150° C. for 4 hours thereby forming a palladium oxide surface coating. The catalyst (2.5 g), 2,6-ditertiary butyl phenol (25 g) and about 0.1 g of NaCO₃ were combined with methanol (50 ml) in a pressure reactor. The reactor was sealed, pressurized to 250 psig with oxygen and heated to about 90° C. After 140 minutes, analysis by gas-liquid chromatography indicated the following weight percent of components in the reaction mixture.

| | |
|---|---|
| 3,3',5,5'-tetratertiary butyl diphenoquinone | 94.0 |
| 2,2',6,6'-tetratertiary butyl-p,p'-biphenol | 1.3 |
| 2,6-ditertiary butyl phenol | 0.5 |
| 2,6-ditertiary butyl-1,4-benzoquinone | 3.7 |

EXAMPLE 3

The reaction conditions of Example 2 were substantially repeated excepting that the catalyst employed was cobalt oxide prepared by precipitating cobalt hydroxide at a pH of about 65. The hydroxide was converted to oxide by calcining at 300° C. for about 1.5 hours. The catalyst was then compressed into pellets and subsequently crushed to a powder.

The catalyst (1.25 g), 2,6-ditertiary butyl phenol (25 g), and about 0.1 g of Na₂CO₃ were combined in 50 ml of methanol. After reaction for 1 hour under 250 psig oxygen at 75° C.–80° C., the reaction mixture was analyzed by gas-liquid chromatography. Results were as follows:

| | |
|---|---|
| 3,3',5,5'-tetratertiary butyl diphenoquinone | 84.2 |
| 2,6-ditertiary butyl phenol | 11.6 |
| 2,4-ditertiary butyl phenol | 1.4 |
| 2,6-ditertiary butyl-1,4-benzoquinone | 2.8 |

EXAMPLE 4

The reaction conditions of Example 2 were substantially repeated excepting that the catalyst employed was a mixture of the oxides of cobalt and copper made by precipitating the hydroxides of an equal molar solution of cobalt nitrate and copper nitrate followed by calcining and pelletizing as previously explained.

The catalyst (1.25 g) was combined with 2,6-ditertiary butyl phenol (25 g) and about 0.1 g of $Na_2CO_3$ in 50 ml of methanol. After heating to 75° C.–80° C. for about 1 hour, the reaction mixture was analyzed and found to have the following composition.

| | |
|---|---|
| 3,3',5,5'-tetratertiary butyl diphenoquinone | 98.1 |
| 2,6-ditertiary butyl phenol | 0.5 |
| 2,4-ditertiary butyl phenol | 0.8 |
| 2,6-ditertiary butyl-1,4-benzoquinone | 0.6 |

EXAMPLE 5

The reaction conditions of Example 4 were substantially repeated employing a precipitated copper oxide catalyst made by the same procedure employed in Examples 3 and 4. After reaction for 1 hour at 75° C.–80° C. under 250 psig oxygen, analysis indicated a conversion of 29.2 percent.

What is claimed is:

1. A process for producing 3,3',5,5'-tetratertiary butyl diphenoquinone comprising contacting 2,6-ditertiary butyl phenol with a heterogeneous oxidative coupling catalyst in the presence of an oxygen-containing gas in a liquid reaction medium comprising methanol.

2. The process according to claim 1 wherein the reaction is conducted at a temperature of from about 30° C. to about 200° C. and at a pressure from atmospheric to about 1000 psig.

3. The process according to claim 2 wherein the temperature is from about 50° C. to about 150° C. and the pressure is from about 100 psig to about 500 psig.

4. The process according to claim 1 or 3 wherein the heterogeneous oxidative coupling catalyst is selected from the group consisting of the elements of groups VIII and IB of the Periodic Table, chromium, molybdenum, zinc and mixtures thereof present in a valence suitable for causing the oxidative coupling of phenolic compounds.

5. The process of claim 4 wherein the heterogeneous oxidative coupling catalyst is a platinum or palladium.

6. The process of claim 4 wherein the catalyst is present in active catalytic species as the metal oxide.

* * * * *